US009717757B1

(12) United States Patent
Gasque, Jr.

(10) Patent No.: US 9,717,757 B1
(45) Date of Patent: Aug. 1, 2017

(54) COMPOSITION AND METHOD TO TREAT AND PREVENT MUSCLE CRAMPING

(71) Applicant: Samuel N. Gasque, Jr., Hendersonville, NC (US)

(72) Inventor: Samuel N. Gasque, Jr., Hendersonville, NC (US)

( * ) Notice: Subject to any disclaimer, the term of this patent is extended or adjusted under 35 U.S.C. 154(b) by 350 days.

(21) Appl. No.: 13/729,102

(22) Filed: Dec. 28, 2012

Related U.S. Application Data

(60) Provisional application No. 61/580,840, filed on Dec. 28, 2011.

(51) Int. Cl.

| | | |
|---|---|---|
| *A61K 33/38* | (2006.01) | |
| *A61K 31/122* | (2006.01) | |
| *A61K 31/352* | (2006.01) | |
| *A61K 31/4166* | (2006.01) | |
| *A61K 31/716* | (2006.01) | |
| *A61K 33/06* | (2006.01) | |
| *A61K 33/14* | (2006.01) | |
| *A61K 36/28* | (2006.01) | |
| *A61K 36/49* | (2006.01) | |
| *A61K 36/88* | (2006.01) | |

(52) U.S. Cl.
CPC ............ *A61K 33/38* (2013.01); *A61K 31/122* (2013.01); *A61K 31/352* (2013.01); *A61K 31/4166* (2013.01); *A61K 31/716* (2013.01); *A61K 33/06* (2013.01); *A61K 33/14* (2013.01); *A61K 36/28* (2013.01); *A61K 36/49* (2013.01); *A61K 36/88* (2013.01)

(58) Field of Classification Search
CPC ........ A61K 33/38; A61K 33/06; A61K 33/14; A61K 36/28; A61K 36/49; A61K 36/88; A61K 31/122; A61K 31/352; A61K 31/4166; A61K 31/716
See application file for complete search history.

(56) References Cited

U.S. PATENT DOCUMENTS

| | | |
|---|---|---|
| 3,852,436 A | 12/1974 | Harich |
| 3,890,212 A | 6/1975 | Harich et al. |
| 4,021,548 A | 5/1977 | Harich et al. |
| 4,021,577 A | 5/1977 | Harich et al. |
| 4,021,578 A | 5/1977 | Harich et al. |
| 5,425,944 A | 6/1995 | Harich |
| 5,631,001 A | 5/1997 | Harich et al. |
| 6,358,516 B1 * | 3/2002 | Harod ........................... 424/401 |
| 7,029,711 B2 | 4/2006 | Farrell |
| 7,670,967 B2 | 3/2010 | Runge et al. |
| 7,704,522 B2 | 4/2010 | Morgan |
| 8,048,447 B2 | 11/2011 | Morgan |
| 2004/0136930 A1 | 7/2004 | Finnegan et al. |
| 2005/0271692 A1 * | 12/2005 | Gervasio-Nugent et al. .............................. 424/401 |
| 2006/0105055 A1 | 5/2006 | Marenick et al. |
| 2007/0134195 A1 * | 6/2007 | Ward et al. ..................... 424/74 |
| 2010/0189675 A1 * | 7/2010 | Pelletier ....................... 424/70.1 |
| 2011/0136210 A1 | 6/2011 | Benjamin et al. |

OTHER PUBLICATIONS

Bounce-Bac, Training and Conditioning., 2009, vol. XIX, No. 5, Advertisment.*
Bounce-Bac 2009, Training and Conditioning., 2009, vol. XIX, No. 5, Hi-Res Advertisment.*
Bounce-Bac 2009 II, Training and Conditioning., 2009, vol. XIX, No. 5, Hi-Res Advertisment.*
Laura. "Citricidal: What is it?" Unifect-GSE-Grapefruit Seed Extract. Sep. 27, 2011. http://citricidal-gse.com/5/grapefruit/.
Pepper, Gary. "What are bioflavonoids and why are the helpful." Aug. 23, 2008. http://www.metabolism.com/2008/08/23/bioflavonoids-helpful.
"The Cramping Towel." iFan Health Products. www.thecrampingtowel.com, no later than Dec. 2011.

* cited by examiner

*Primary Examiner* — Teresa E Knight
(74) *Attorney, Agent, or Firm* — Ben Schroeder Law, PLLC

(57) ABSTRACT

A method of treating muscle cramps and muscle pain, and to relieve swelling in and around muscles after strenuous physical activity is provided, whereby an aqueous composition is applied topically to the skin overlying the affected muscles, the composition has dissolved, suspended or dispersed therein (a) an anti-inflammatory agent; (b) an agent that stimulates or promotes cell growth; and (c) an agent that enhances or stimulates the skin's immune system, wherein components (a), (b) and (c) are different.

16 Claims, No Drawings

COMPOSITION AND METHOD TO TREAT AND PREVENT MUSCLE CRAMPING

This invention is directed to a composition and method of topical application of the composition to treat and prevent muscle cramping, muscle pain and swelling in and around muscle tissue. Also, the invention is useful in treating and preventing skin infections, as well as protecting the skin.

BACKGROUND OF THE INVENTION

The exact cause of muscle cramps occurring during or after exercise (referred to as "exercise associated muscle cramps" or "EAMC") remains largely unknown. Factors attributed to an increase likelihood of developing a muscle cramp include dehydration, electrolyte depletion and muscle fatigue. One theory attributes cramps to altered neuromuscular control due to the development of muscle fatigue. Medications that alter the balance of a person's electrolytes have, in some cases, been associated with an increased risk of cramping. Treatment typically involves stopping the physical activity and stretching and massaging the effected muscles.

Cramp 911® is a topical homeopathic product that claims to relieve muscle cramps. The active ingredients are listed as magnesium sulfate 6×H.P.U.S. and cuprum metallicum 6×H.P.U.S., with "6x" representing the dilution strength of 1 part per million. According to the Cramp 911 website, homeopathy uses the therapeutic effects of substances by attenuating their toxicity through the use of very small doses right until the "infinitesimal" level.

U.S. Pat. No. 6,358,516 B1 discloses a multi-ingredient composition to provided one-step cleansing, conditioning and treating a person's skin. There is no disclosure of using such a composition to treat or prevent muscle cramps.

SUMMARY OF THE INVENTION

The present invention is directed to a method of topical application of a composition to treat and prevent muscle cramping, muscle pain and swelling in and around muscle tissue. The method and composition are particularly useful for treating exercise associated muscle cramps.

The composition contains a combination of active ingredients, including an anti-inflammatory agent, a cell-growth promoting agent, and an immune system enhancing agent. Some ingredients possess one or more of the foregoing properties, and in one embodiment of the invention, a synergistic effect is achieved by selecting a different agent from each of the foregoing categories. The composition may further comprise one or more of an antimicrobial agent, absorption facilitating agent, humectants and emollients, and/or free radical scavenging agents. Additional optional ingredients to enhance performance, stabilize or preserve the composition include surfactants, preservatives, anti-foaming agents and fragrances.

An alternative composition useful in the invention has as its primary ingredient a bioflavonoid derived quaternary compound. For example, the compound may be a citrus derived bioflavonoid, including a grapefruit seed extract, such as Citricidal®.

Another alternative composition useful in the present invention is a combination of *arnica montana* and a bioavailable source of magnesium, such as magnesium laurate, magnesium sulfate or magnesium oil ($MgCl_2$). A skin penetrant, to facilitate absorption of the composition into a person's dermis may be included, such as dimethyl isosorbide. Optionally, a biocompatible preservative is included in the composition.

The composition may be aqueous-based, that is, the ingredients are dissolved, suspended or dispersed in water. For example, the composition may contain from 40 to 95% water.

The composition can be topically applied to the skin in the area where muscle cramping, soreness and/or swelling is sought to be treated or prevented. The composition may be applied by spray or foam applicator, roll-on applicator, by hand, or liquid impregnated substrate. For example, a substrate, such as a disposable towel, may be impregnated with the composition and the composition rubbed or dabbed on the surface of the skin.

The composition is particularly useful to treat muscle cramp and pain, or to relieve swelling in and around muscles that occur during or within 2, 4 or even 24 hours or more of strenuous physical activity. For example, an athlete suffering from muscle cramps or pains during a sporting event can receive a topical application of the composition to the skin in and around the affected area and resume activity. In another example, pain and swelling subsequent to strenuous physical activity can be treated by a topical application of the composition to the skin in and around the affected area. In yet another example, the composition may be applied to treat cramps that occur subsequent to strenuous physical exercise.

The method of treatment is not limited to exercise associated muscle cramps, pain and swelling. Rather, the method may be used to treat anyone experiencing the foregoing symptoms, regardless of their origin.

The composition of the present invention may be formulated to provide additional benefits to the performance of the composition.

In one embodiment of the invention, a bioavailable source of magnesium is added to the composition, such as magnesium laurate, magnesium sulfate or magnesium oil ($MgCl_2$). The concentration of magnesium may be up to 5% of the composition, by weight.

In another embodiment of the invention, Coenzyme $Q_{10}$ is included in the composition as a skin protector. Optionally, chamomile extract may be included with Coenzyme $Q_{10}$ to unclog skin pores.

In another embodiment of the invention, chamomile extract is included in the composition to soothe the skin and reduce swelling.

In another embodiment of the invention, white oak bark extract is included in the composition to help shrink tissues. *Calendula* extract may optionally be added to the composition to alleviate skin problems, such as sunburn, and to promote healing of cuts, bruises, burns and rashes and/or to heal scars.

In yet another embodiment of the invention, speedwell extract (*Veronica officinalis*) is included in the composition to reduce swelling and alleviate itches.

Any of the above compositions may be formulated to be surfactant free, to avoid negative effects, such as dry skin, inflammation and reduction of the barrier properties of the skin. Further, if any of the above compositions include a preservative, natural preservatives, such as NataPres™, are preferred over synthetic compounds such as EDTA and alkyl-parabens.

The composition may be formulated to contain all natural ingredients (100% natural ingredients) or natural ingredients (at least 95% natural ingredients). While some organizations certifying products as being "natural" exclude the use of synthetic fragrances, for example the Natural Ingredient Resource Center (NIRC), in the present invention, the composition may incorporate a synthetic fragrance up to 1% by weight and meet the natural definition, provided at least 95% of the ingredients are natural according to the NIRC criteria.

DETAILED DESCRIPTION OF THE INVENTION

Without limiting the scope of the invention, the preferred embodiments and features are hereinafter set forth. All of the United States patents, which are cited in the specification, are hereby incorporated by reference. Unless otherwise indicated, conditions are 25° C., 1 atmosphere of pressure and 50% relative humidity, concentrations are by weight, and molecular weight is based on weight average molecular weight. Unless otherwise indicated, alkyl groups are $C_1$-$C_{24}$.

The basic composition of the present invention is made up a combination of ingredients selected from the following:
(a) Anti-inflammatory agents, including but not limited to aloe vera, allantoin (glyoxyldiureide or 5-ureidohydantoin), beta glucan, *arnica montana* flower extract and combinations thereof;
(b) Agents that stimulate or promote cell growth, including but not limited to aloe vera, allantoin, beta glucan, and quaternary compounds derived from bioflavonoids, such as Citricidal®, a citrus derived bioflavonoid.
(c) Agents that enhance and/or stimulate the skin's immune system and/or help provide a secondary immune system, including but not limited to aloe vera, allantoin, beta glucan, colloidal silver, quaternary compounds derived from bioflavonoids, such as Citricidal®, and combinations thereof.
(d) Fast-acting, skin-compatible antimicrobial agents (i.e., agents that are effective against bacteria, viruses, yeasts, and/or fungi), including but not limited to colloidal silver, quaternary compounds derived from bioflavonoids, such as Citricidal®, pycnogenol, compounds derived from flavanols, such as grape seed extract, antibiotics, and combinations thereof, in effective amounts to kill infectious bacteria, viruses, yeasts, and fungi. The colloidal silver is preferably formulated with particles that are small enough to penetrate the dermis (approximately 0.005-0.02 microns; more preferably, approximately 0.01-0.1 microns).
(e) Agents that, by their particle size and/or function, facilitate absorption into the second layer of the skin or dermis, including but not limited to beta glucan, aloe vera, colloidal silver, allantoin, Citricidal®, dimethyl isosorbide and combinations thereof.
(f) Agents that scavenge free radicals and help detoxify the skin, including but not limited to quaternary compounds derived from bioflavonoids, such as Citricidal®, beta glucan, allantoin, vitamin E (tocopherol), pycnogenol, compounds derived from flavanols, such as grape seed extract, and combinations thereof.
(g) Agents that promote and/or stimulate new skin growth and skin healing, including but not limited to aloe vera, allantoin, quaternary compounds derived from bioflavonoids, such as Citricidal®, beta glucan, pharmaceuticals, and combinations thereof.
(h) Compatible humectants and emollients, including but not limited to aloe vera, allantoin, vitamin E (tocopherol), beta glucan, cocamidopropyl betaine, dimethicone PEG-8 Meadowfoamate, and combinations thereof.
(i) Biocompatible preservatives, including NataPres®, alkly-parabens, such as methylparaben and propylparaben, ethylenediamine-tetraacetic acid (EDTA), phenoxyethanol, like agents, and combinations thereof.
(j) emulsifiers, as necessary to disperse any of the ingredients in an aqueous medium. Examples include lecithin, emulsifying wax, cetearyl alcohol, polysorbate 20, and ceteareth 20. The emulsifier may be a surfactant, such as amphoteric surfactants (i.e., surfactants having the capacity of behaving either as an acid or a base), cocamidopropyl betaine, alkyl polyglucosides, lauryl glucoside, and combinations thereof. In some instances, the negative effects of surfactants, such as dry skin, inflammation and reduction of the barrier properties of the skin, can be avoided by employing the minimum amount of emulsifier necessary to achieve a stable emulsion, that is, at least 30 days without observable separation.
(k) Biocompatible fragrances, including but not limited to natural orange, lemon, lavender, and combinations thereof.
(l) Other beneficial agents, including but not limited to those containing vitamins and vitamin precursors (vitamin A, carotene, cryptoxanthin, retinol, 3-dehydroretinol, vitamin C (ascorbic acid), vitamin E (tocopherol), etc.), herbs (chamomile, lavender, *ginseng*, ginkgo, etc.), antioxidants, collagens, pH-balancing agents, and combinations thereof.
(m) Skin-compatible anti-foaming agents such as silicone-based antifoaming agents, dimethicone copolyol, and the like, may optionally be used, as necessary to improve processing.

Depending on the application, the composition may be provided in various forms, for example, in the form of a cream, ointment, liniment, paste, gel or liquid. Accordingly, the form of the composition may be modified by the use of thickening agents, gelling agents, fillers, emulsifiers, various solid to liquid ratios, and various solvent to ingredient ratios. Suitable thickening agents include xantham gum and cellulose derived thickening agents, such as hydroxyethylcellulose and methyl cellulose.

The composition may be aqueous-based, that is, the ingredients are dissolved, suspended or dispersed in water. For example, the composition may contain from 40 to 95% water, or for some applications from 70 to 90% water.

The pH of the composition is preferably relatively close to that of human skin, that is, approximately 4.5-6.7 although compositions with a pH outside this range may also be useful. The composition is naturally pH-balanced when formulated with selected ingredients as described below. However, pH-balancing agents may be added if desired.

The composition may be sterilized by irradiation, such as by exposure to gamma radiation. For example, a textile fabric may be saturated with the composition, packaged and then subjected to gamma radiation to provide a sterile product.

The basic composition made according to the invention contains at least one ingredient selected from each of groups (a)-(c) and at least one ingredient selected from one of groups (d)-(j), in an aqueous solution and/or dispersion. Preferably, the composition includes at least five ingredients in addition to water: at least one ingredient from each of groups (a)-(c), and at least two different ingredients from one of groups (d)-(j). Additional ingredients such as skin-compatible preservatives and fragrances may be added if desired. In one embodiment of the invention, each of the ingredients representing one of groups (a)-(m) is different from the other ingredients representing groups (a)-(m) in the composition.

Some ingredients such as aloe vera, allantoin, and beta glucan exhibit a spectrum of useful effects, thus, these ingredients may appear in more than one of above-described groups (a)-(m). However, in a composition formulated according to one embodiment of the invention, each of the selected ingredients is preferably different from the other ingredients so that each selected ingredient is present in sufficient quantity to perform its function or functions, referred to generally as being present in an "effective amount." Similar considerations apply to all ingredients selected for the composition. The various ingredients in the composition are provided in sufficient quantities and combinations to be effective, and to take advantage of their synergistic effects (when combined according to the invention) without detrimental side effects. All of the ingredients of the composition are selected for their overall compatibility with skin and tissue health.

Suitable compositions may be found in U.S. Pat. No. 6,358,516, which is incorporated by reference in its entirety, herein. Also included within the scope of the invention is a modification of the compositions disclosed in U.S. Pat. No. 6,358,516 by substituting natural ingredients for the synthetic ingredients to provide a natural product, that is, a product having at least 95% or even 100% natural ingredients.

In one embodiment of the invention, the composition contains less than 1% surfactants, preferably less than 0.5% surfactants, most preferably the composition is free of surfactants. In another embodiment of the invention, the composition does not contain an anti-foaming agent.

The following formulations are believed to be effective in meeting the objectives of the present invention, that is, topical application of the composition to treat and prevent muscle cramping, muscle pain and swelling in and around muscle tissue.

Formulation 1
    Water
    Aloe vera
    Citricidal®
    Allantoin
    Colloidal silver
    Lauryl glucoside
    Beta glucan
    Abil B—silicone surfactant
    NataPres®
    Fragrance
    Vitamin E The formulation may contain approximately 40 to 95% water, 0.1 to 7% aloe vera, 0.1 to 1% allantoin and 0.1 to 6% beta glucan. The remaining ingredients may be present in amounts of from 0.001 to 7%.

Formulation 2—Antifoaming Agent Free
    Water
    Aloe vera
    Citricidal®
    Cocamidopropyl betaine
    Allantoin
    Colloidal silver
    Lauryl glucoside
    Beta glucan
    NataPres®
    Fragrance
    Vitamin E The formulation may contain approximately 40 to 95% water, 0.1 to 7% aloe vera, 0.1 to 1% allantoin and 0.1 to 6% beta glucan. The remaining ingredients may be present in amounts of from 0.001 to 7%.

Formulation 3—Surfactant Free
    Water
    Aloe vera
    Citricidal®
    Cocamidopropyl betaine
    Allantoin
    Colloidal silver
    Beta glucan
    NataPres®
    Fragrance
    Vitamin E The formulation may contain approximately 40 to 95% water, 0.1 to 7% aloe vera, 0.1 to 1% allantoin and 0.1 to 6% beta glucan. The remaining ingredients may be present in amounts of from 0.001 to 7%. Emulsifiers may be added, as necessary, to achieve a stable composition.

Formulation 4—Bioavailable Magnesium

The basic composition contains at least one ingredient selected from each of groups (a)-(c) and at least one ingredient selected from one of groups (d)-(j), in an aqueous solution and/or dispersion. In addition to the basic composition, a bioavailable source of magnesium is added to the composition, such as magnesium laurate, magnesium sulfate or magnesium oil ($MgCl_2$). The concentration of magnesium may be up to 5% of the composition, by weight. An example of a suitable formulation is:
    Water
    Aloe vera
    Citricidal®
    Cocamidopropyl betaine
    Allantoin
    Colloidal silver
    Beta glucan
    $MgCl_2$
    NataPres®
    Fragrance
    Vitamin E The formulation may contain approximately 40 to 95% water, 0.1 to 7% aloe vera, 0.1 to 1% allantoin and 0.1 to 6% beta glucan. The remaining ingredients may be present in amounts of from 0.001 to 7%. Emulsifiers may be added, as necessary, to achieve a stable composition.

Formulation 5—Coenzyme $Q_{10}$

The basic composition contains at least one ingredient selected from each of groups (a)-(c) and at least one ingredient selected from one of groups (d)-(j), in an aqueous solution and/or dispersion. In addition to the basic composition, Coenzyme $Q_{10}$ is included in the composition as a skin protector. The concentration of Coenzyme $Q_{10}$ may be up to 5% of the composition, by weight. Optionally, an effective amount of chamomile extract may be included with Coenzyme $Q_{10}$ to unclog skin pores.
    Water
    Aloe vera
    Citricidal®
    Cocamidopropyl betaine
    Allantoin
    Colloidal silver
    Beta glucan
    NataPres®
    Fragrance
    Vitamin E
    Coenzyme $Q_{10}$ The formulation may contain approximately 40 to 95% water, 0.1 to 7% aloe vera, 0.1 to 1% allantoin and 0.1 to 6% beta glucan. The remaining ingredients may be present in amounts of from 0.001 to 7%. Emulsifiers may be added, as necessary, to achieve a stable composition.

Formulation 6—Chamomile Extract

The basic composition contains at least one ingredient selected from each of groups (a)-(c) and at least one ingredient selected from one of groups (d)-(j), in an aqueous solution and/or dispersion. In addition to the basic composition, chamomile extract is included in the composition to soothe skin and reduce swelling. The concentration of chamomile extract may be up to 5% of the composition, by weight.

Water
Aloe vera
Citricidal®
Cocamidopropyl betaine
Allantoin
Colloidal silver
Beta glucan
NataPres®
Fragrance
Chamomile extract
Vitamin E The formulation may contain approximately 40 to 95% water, 0.1 to 7% aloe vera, 0.1 to 1% allantoin and 0.1 to 6% beta glucan. The remaining ingredients may be present in amounts of from 0.001 to 7%. Emulsifiers may be added, as necessary, to achieve a stable composition.

Formulation 7—White Oak Bark Extract

The basic composition contains at least one ingredient selected from each of groups (a)-(c) and at least one ingredient selected from one of groups (d)-(j), in an aqueous solution and/or dispersion. In addition to the basic composition, white oak bark extract is included in the composition to help shrink tissues. The concentration of white oak bark extract may be up to 5% of the composition, by weight. Optionally, an effective amount of *calendula* extract may be included with white oak bark extract, to alleviate skin problems, such as sunburn, and to promote healing of cuts, bruises, burns and rashes and/or to heal scars.

Water
Aloe vera
Citricidal®
Cocamidopropyl betaine
Allantoin
Colloidal silver
Beta glucan
NataPres®
White oak bark extract
*Calendula* extract
Fragrance
Vitamin E The formulation may contain approximately 40 to 95% water, 0.1 to 7% aloe vera, 0.1 to 1% allantoin and 0.1 to 6% beta glucan. The remaining ingredients may be present in amounts of from 0.001 to 7%. Emulsifiers may be added, as necessary, to achieve a stable composition.

Formulation 8—*Veronica officinalis* (Speedwell)

The basic composition contains at least one ingredient selected from each of groups (a)-(c) and at least one ingredient selected from one of groups (d)-(j), in an aqueous solution and/or dispersion. In addition to the basic composition, speedwell extract (*Veronica officinalis*) is included in the composition to reduce swelling and alleviate itches. The concentration of speedwell extract may be up to 5% of the composition, by weight.

Water
Aloe vera
Citricidal®
Cocamidopropyl betaine
Allantoin
Colloidal silver
Beta glucan
NataPres®
Speedwell extract
Fragrance
Vitamin E The formulation may contain approximately 40 to 95% water, 0.1 to 7% aloe vera, 0.1 to 1% allantoin and 0.1 to 6% beta glucan. The remaining ingredients may be present in amounts of from 0.001 to 7%. Emulsifiers may be added, as necessary, to achieve a stable composition.

Formulation 9—*Arnica Montana*

In one embodiment, the composition contains aloe vera, beta glucan and *arnica montana* as active ingredients in concentrations ranging from 1 to 10 weight % each. Additionally, the composition may comprise one or more, preferably at least two or more, and most preferably at least three or more of an agent to increase penetration of the composition into the dermis of a person, a preservative, an emulsifier, an emollient, an antimicrobial and a bioavailable source of magnesium, in concentrations ranging from 0.01 to 8 weight % each. The composition may comprise from 40 to 95% water.

By way of example, the composition may contain the following ingredients:

Water
Aloe vera
*Arnica Montana* Flower Extract
Beta Glucan
Dimethyl Isosorbide
*Vitis Vinifera* (Grape) Seed Extract
Phenoxyethanol
Polysorbate 20
Allantoin
Dimethicone PEG-8 Meadowfoamate
Tocopherol
Xantham Gum
Magnesium Chloride
Colloidal Silver Formulation 10—*Arnica Montana* and Bioavailable Source of Magnesium It is believed that a synergistic effect in terms of the treatment and prevention of muscle cramping, muscle pain and swelling in and around muscle tissue, can be achieved by providing a composition having an effective amount of *arnica montana* and a bioavailable source of magnesium, such as magnesium laurate, magnesium sulfate or magnesium oil ($MgCl_2$). By way of example, the *arnica montana* may be present in a concentration of from 1 to 15 weight % and the magnesium compound is present in a concentration of from 0.01 to 8 weight %. The composition may include a skin penetrant, to facilitate absorption into the second layer of the skin or dermis, a biocompatible preservative, and, depending on the desired consistency of the composition, a thickening agent. The composition may comprise from 40 to 95% water.

Water
*Arnica montana*
Magnesium sulfate
Dimethyl isosorbide
Phenoxyethanol

Formulation 11—Bioflavonoid Derived Quaternary Compound

It is believed that the objectives of the invention, that is, the treatment and prevention of muscle cramping, muscle pain and swelling in and around muscle tissue, can also be met by providing a composition having a bioflavonoid derived quaternary compound as its primary ingredient. The bioflavonoid derived quaternary compound may be a citrus derived bioflavonoid, such a grapefruit seed extract. Thus, while positive results have been found employing compositions containing at least one ingredient selected from each of groups (a)-(c), an alternative formulation within the scope of the invention is a composition having an effective concentration of a bioflavonoid derived quaternary compound. As noted above, such compounds are believed to offer a broad spectrum of useful properties, including promotion of cell growth, enhancement or stimulation of the skin's immune system, antimicrobial activity, and scavenging free radicals. By way of example, the bioflavonoid derived quaternary compound may be present in the composition in a concentration of from 0.5 to 75% by weight, preferably 1 to 15% by weight, in a solvent carrier, such as water, alcohol or organic solvent, such as glycerin.

Example: water 95%/Citricidal 5%.

Methods of Use

The compositions described herein can be used to treat and prevent muscle cramps, in particular exercise associated muscle cramps, as well as to treat and prevent muscle pain and swelling in and around muscle tissue. The composition may be topically applied to the skin in the area around the muscle tissue sought to be treated before, during or after athletic exercise. For example, the calf muscles are often subject to muscle cramps, and the composition can be applied topically to the skin overlaying the calf muscles to effect treatment.

For treatment to prevent muscle cramping and to reduce muscle pain and swelling, it is recommended to apply the composition to the skin in the relevant area of the muscle within 1 hour before the intended athletic activity or event found to give rise to muscle cramping, pain or swelling.

The composition may be applied to alleviate muscle cramping, pain or swelling as it occurs. For example, a muscle cramp during athletic activity or a muscle cramp occurring during the middle of the night can be treated with prompt application of the composition to a person's skin around the affected muscle tissue. For best results, the treatment should be applied immediately after or within 5 minutes of a cramping event. Nevertheless, good results can be achieved by applying the treatment within 10 minutes or even within 20 minutes after the cramping event.

The composition is particularly useful to treat muscle cramp and pain, or to relieve swelling in and around muscles that occur within 2, 4 or even 24 hours after strenuous physical activity. For example, the composition may be topically applied (i) immediately following an athletic event; (ii) after the athlete has cooled down and showered; or (iii) as part of a post-workout massage. In another example, a person suffering from pain and swelling in and around muscle tissues may apply the subject composition one day or even two days after an athletic workout.

The use of the composition is not limited to athletes, however, and anyone experiencing muscle cramping, pain and swelling in and around muscle tissue may find relief through topical application of the composition of the present invention. By way of example, the following conditions may be helped by application of the composition: night leg cramps, bruised muscle tissue and muscle strains and tears.

The composition may be applied by spray or foam applicator, roll-on applicator, by hand, or with a saturated substrate. For example, a substrate, such as a towel, may be impregnated with the composition and the composition rubbed or dabbed on the surface of the skin. The composition can be formulated to achieve a wide range of consistencies, and may be applied in the form of a cream, ointment, liniment, paste, gel or liquid. Good effects are realized when the composition is gently massaged into in the skin surrounding the muscles to be treated.

In addition to the aforementioned benefits of treating and preventing muscle cramping, muscle pain and swelling in and around muscle tissue, the identified compositions exhibit antimicrobial properties. Accordingly, topical application of the composition to a person's skin is believed to effectively treat and prevent infection from microbial pathogens, including viruses, bacteria and fungi. By way of example, the composition could be applied to an athlete's exposed skin, prior to an athletic event, to prevent infections that otherwise might arise from body contact. In another example, an athlete who has been involved in a bicycle crash can receive a topical application of the composition to any open scrapes on the skin, to prevent infections.

Also within the scope of the present invention is a method of topical application to the skin of the aforementioned compositions as a general skin protectant. Particularly useful are compositions containing one or more of the following features: the composition contains an effective concentration of Coenzyme $Q_{10}$; the composition is surfactant free; the composition is at least 95% natural products (excluding up to 1% synthetic fragrance) or even comprises 100% natural ingredients.

The invention may be further understood by reference to the following claims.

What I claim is:

1. A method of treating a muscle cramp, comprising the step of topically applying an aqueous composition to a person's skin overlaying the area of a muscle cramp, within 20 minutes of the occurrence of the muscle cramp, whereby the aqueous composition has dissolved, suspended or dispersed therein (a) an anti-inflammatory agent; (b) an agent that stimulates or promotes cell growth selected from the group consisting of aloe vera, allantoin, beta glucan, and quaternary compounds derived from bioflavonoids; and (c) an agent that enhances or stimulates the skin's immune system selected from the group consisting of aloe vera, allantoin, beta glucan, colloidal silver, and quaternary compounds derived from bioflavonoids, wherein the composition comprises a bioavailable source of magnesium and comprises *arnica montana* flower extract; wherein the composition is surfactant free; and wherein components (a), (b) and (c) are different.

2. The method of claim 1, wherein the anti-inflammatory agent is selected from the group consisting of aloe vera, allantoin and beta glucan, the agent that stimulates or promotes cell growth is selected from the group consisting of aloe vera, allantoin, beta glucan, and quaternary compounds derived from bioflavonoids, and the agent that enhances or stimulates the skin's immune system is selected from the group consisting of aloe vera, allantoin, beta glucan, colloidal silver, quaternary compounds derived from bioflavonoids.

3. The method of claim 1, further comprising at least one agent selected from group (d)-(j), wherein (d) is an antimicrobial agent; (e) is a skin absorption facilitating agent; (f) a free radical scavenging agent; (g) is an agent that promotes skin healing; (h) is a humectants or emollient agent; (i) is a biocompatible preservative agent; and (j) is an emulsifier, wherein the at least one agent is different from components (a)-(c).

4. The method of claim 3, further comprising at least two agents selected from groups (d)-(j), wherein the at least two agents are different from each other and different from components (a)-(c).

5. The method of claim 1, wherein the composition is topically applied within 10 minutes of the occurrence of the muscle cramp.

6. The method of claim 1, wherein the composition comprises from 40 to 95 weight % water.

7. The method of claim 1, wherein the composition comprises a citrus derived bioflavonoid quaternary compound.

8. The method of claim 1, wherein the source of magnesium is selected from the group consisting of magnesium laurate, magnesium sulfate and magnesium chloride.

9. The method of claim 1, wherein the composition comprises colloidal silver having a particle size capable of penetrating the dermis of a person.

10. The method of claim 1, wherein the composition comprises Coenzyme $Q_{10}$.

11. The method of claim 1, wherein the composition comprises at least 95 weight % natural ingredients.

12. The method of claim 1, wherein the composition further comprises a natural preservative.

13. A method of treating muscle cramps, muscle pain and muscle swelling, comprising the step of topically applying an aqueous composition to a person's skin overlaying the area of a muscle, within 24 hours of strenuous physical activity, whereby the aqueous composition has dissolved, suspended or dispersed therein (a) an anti-inflammatory agent; (b) an agent that stimulates or promotes cell growth selected from the group consisting of aloe vera, allantoin, beta glucan, and quaternary compounds derived from bioflavonoids; and (c) an agent that enhances or stimulates the skin's immune system selected from the group consisting of aloe vera, allantoin, beta glucan, colloidal silver, and quaternary compounds derived from bioflavonoids, wherein the composition comprises a bioavailable source of magnesium and comprises *arnica montana* flower extract and wherein the composition is surfactant free; and wherein components (a), (b) and (c) are different.

14. The method of claim 13, wherein the composition further comprises colloidal silver having a particle size capable of penetrating the dermis of a person.

15. The method of claim 14, wherein the composition further comprises dimethyl isosorbide as a skin absorption facilitating agent.

16. The method of claim 13, wherein the composition further comprises a natural preservative.

* * * * *